United States Patent

Henson et al.

[11] 4,336,384
[45] Jun. 22, 1982

[54] PREPARATION OF 4-AMINO-3,5,6-TRICHLOROPICOLINIC ACID

[75] Inventors: Edwin R. Henson, Lake Jackson; David J. Koranek, Clute, both of Tex.

[73] Assignee: The Dow Chemical Company, Midland, Mich.

[21] Appl. No.: 257,308

[22] Filed: Apr. 23, 1981

[51] Int. Cl.³ .................. C07D 213/55; C07D 213/57
[52] U.S. Cl. ..................... 546/327; 546/286; 546/326
[58] Field of Search ................. 546/327, 326

[56] References Cited

U.S. PATENT DOCUMENTS 3,285,925  11/1966  Johnston et al. ............ 546/286
3,325,503   6/1967  Bimber ........................ 546/287

FOREIGN PATENT DOCUMENTS 445662  5/1974  U.S.S.R. ...................... 546/327

OTHER PUBLICATIONS

Wagner & Zook, "Synthetic Organic Chemistry", p. 412, Wiley & Sons Pub., (1953).
Morrison & Boyd "Organic Chemistry," pp. 586-589, Allyn & Bacon Pub. (1973).
McElvain et al., Journal of American Chemical Society, vol. 63, p. 2283, (1941).

*Primary Examiner*—Alan L. Rotman
*Attorney, Agent, or Firm*—John M. Sanders

[57] ABSTRACT

In a new method of producing 4-amino-3,5,6-trichloropicolinic acid 3,4,5,6-tetrachloropicolinonitrile is reacted with ammonium hydroxide, preferably at about 130° C. to about 160° C. The free acid is precipitated upon acidification of the reaction mixture and may be recovered therefrom.

7 Claims, No Drawings

PREPARATION OF 4-AMINO-3,5,6-TRICHLOROPICOLINIC ACID

BACKGROUND OF THE INVENTION

1. Field of the Invention

This invention relates to a method of preparing 4-amino-3,5,6-trichloropicolinic acid, in a one step process of aminating and hydrolyzing 3,4,5,6-tetrachloropicolinonitrile.

2. Description of Prior Art

It is known that 4-amino-3,5,6-trichloropicolinic acid is prepared by a two-step method where heptachloro-2-picoline is aminated with anhydrous liquid ammonia to form 4-amino-hexachloro-2-picoline, an intermediate product that is isolated, and which is in turn hydrolyzed with sulfuric acid to form 4-amino-3,5,6-trichloropicolinic acid. See, for example, Russian Pat. No. 445,662.

Russian Pat. No. 445,662 also teaches a method of producing 4-amino-3,5,6-trichloropicolinic acid by treating heptachloro-2-picoline with aqueous ammonia at a temperature of from 120°–180° C. resulting in the formation of the ammonium salt of 4-amino-3,5,6-trichloropicolinic acid which is then acidified to obtain the free acid.

It is also suggested by Morrison and Boyd, *Organic Chemistry*, 3rd Ed., New York University, 1973, p. 586, that aromatic nitriles may be hydrolyzed with an acid or a base to form the corresponding carboxylic acid.

SUMMARY OF THE INVENTION

In accordance with the present invention 4-amino-,3,5,6-trichloropicolinic acid is prepared by contacting 3,4,5,6-tetrachloropicolinonitrile with ammonium hydroxide and then acidifying the reaction mixture to precipitate said 4-amino-3,5,6-trichloropicolinic acid.

The compound prepared by the present invention is useful as a herbicide and is described in U.S. Pat. No. 3,285,925.

DESCRIPTION OF THE PREFERRED EMBODIMENTS

When preparing 4-amino-3,5,6-trichloropicolinic acid by the present invention, 3,4,5,6-tetrachloropicolinonitrile (hereinafter referred to as picolinonitrile) is reacted with ammonium hydroxide. During the reaction, it is advantageous to keep the reactants under constant agitation. The 3,4,5,6-tetrachloropicolinonitrile used as the starting material is a known compound and its preparation is taught in U.S. Pat. No. 3,325,503.

The exact temperature at which the reaction is conducted is not critical but generally is from about 0° C. to about 200° C. and is preferably from about 130° C. to about 160° C.

While the exact concentration and amount of ammonium hydroxide used in the present invention is not critical, it is advantageous to utilize an amount of $NH_4OH$ in excess of the stoichiometric amount needed to react with the amount of 3,4,5,6-tetrachloropicolinonitrile present in the reaction mixture. It is preferred to bring together the $NH_4OH$ and the picolinonitrile in a molar ratio in the range of about 1.5 to about 20 moles of $NH_4OH$ (as ammonia) per mole of picolinonitrile. The use of an appropriate ratio of reactants is shown by the 10 g (0.041 moles) of 3,4,5,6-tetrachloropicolinonitrile with 26 ml of 28% ammonium hydroxide (0.43 moles ammonia).

The method of the present invention is most conveniently conducted in a contained environment (sealed vessel), such as, for example, an autoclave or a Parr bomb, to prevent the escape of ammonia vapor. Raising the reaction temperature causes the pressure to increase in the contained environment where the reaction is taking place.

The reaction time varies inversely with the temperature, i.e., the higher the temperature the faster the reaction and the shorter the reaction time required. When employing a temperature in the preferred range of from about 130° C. to about 160° C. the reaction usually takes from about ½ to about 24 hours to be completed.

After the reaction is complete the 4-amino-3,5,6-trichloropicolinic acid is recovered in solid crystalline form by methods, such as, acidification, and may be purified by known conventional techniques if desired.

The following examples illustrate the present invention but, as such, should not be construed as limitations upon the overall scope of the same.

EXAMPLE 1

Five grams (g) (0.021 moles) of 3,4,5,6-tetrachloropicolinonitrile and 80 milliliters (ml) of 28% aqueous ammonium hydroxide (1.32 moles of ammonia) were added to a 250 ml Berghof ® brand polytetrafluoroethylene lined autoclave equipped with a stir bar. The autoclave was sealed, placed in a heating mantle with a Valco ® brand proportional type heating controller and set on a stir plate. The heater and stirrer were started and approximately one hour was allowed for heat-up. The reaction was carried out at about 140° C. for about 16.5 hours. The pressure at 140° C. due to ammonia was 155 psig. After the reaction period the autoclave, when cool, was removed from the heating mantle and the contents washed out with distilled water into a flask. The diluted aqueous reaction mixture was nitrogen sparged with warming to remove dissolved ammonia. Insolubles were filtered off, and the filtrate acidified with hydrochloric acid. The free picolinic acid which formed, separated as crystals and was recovered by filtration. The yield of crude 4-amino-3,5,6-trichloropicolinic acid was 75% of theoretical.

EXAMPLE 2

3,4,5,6-Tetrachloropicolinonitrile (54.8 g) (0.226 moles) and 250 ml of 30% ammonium hydroxide (4.41 moles of ammonia) were added to a 2 liter SS Parr ® bomb equipped with a stirrer.

The reaction mixture was heated with stirring to about 150° C. in about one hour. This temperature was maintained for about ½ hour and then the reaction mixture was cooled with a coil containing glycol and water. The temperature was brought down to about 21° C. The bomb was then vented and purged with nitrogen. 4-Amino-3,5,6-trichloropicolinic acid was then recovered in a manner similar to that described in Example 1.

EXAMPLE 3

To a two liter Parr autoclave, equipped with a stirrer, were added 100 g (0.413 moles) of finely ground 3,4,5,6-tetrachloropicolinonitrile (96% pure), 98 g of ammonia (5.77 moles) and 802 g of water. The autoclave was sealed and then heated with constant stirring to 140° C. for 8 hours after which the autoclave was removed from the heat and excess pressure was released. The pressure at the end of the reaction period, due to ammonia, was 100 psig. The contents of the autoclave were washed into a large beaker where it was purged with nitrogen and warmed overnight to remove ammonia from solution. The solution was then acidified with sulfuric acid causing the desired picolinic acid product to precipitate. The precipitate was recovered and dried. The 4-amino-3,5,6-trichloropicolinic acid product was recovered in a yield of 61.7% of theoretical.

EXAMPLE 4

Substantially the same procedure as that employed in Example 3 was carried out except the reaction temperature was 155° C. and the reaction time was 4 hours. The yield of 4-amino-3,5,6-trichloropicolinic acid obtained was 58.07% of theoretical.

EXAMPLE 5

Substantially the same procedure as that employed in Example 3 was carried out except the amount of ammonia added was 387 g (22.76 moles) in 504 g of water (28 moles). The reaction temperature was 150° C. and the reaction time was 4 hours. The yield of 4-amino-3,5,6-trichloropicolinic acid obtained was 32.50% of theoretical.

EXAMPLE 6

Substantially the same procedure as that employed in Example 3 was carried out except the amount of ammonia added was 45 g (2.6 moles) in 855 g of water (47.5 moles). The reaction temperature was 150° C. and the reaction time was 4 hours. The yield of 4-amino-3,5,6-trichloropicolinic acid obtained was 50.57% of theoretical.

We claim:

1. A method of preparing 4-amino-3,5,6-trichloropicolinic acid which comprises reacting 3,4,5,6-tetrachloropicolinonitrile with ammonium hydroxide and acidifying the so-formed reaction mixture to precipitate said 4-amino-3,5,6-trichloropicolinic acid.

2. The method of claim 1 wherein the concentration of said ammonium hydroxide is in the range of from about 5 to about 30 percent by weight of ammonia in water.

3. The method of claim 1 wherein said method is carried out a a temperature of from about 0° C. to about 200° C.

4. The method of claim 3 wherein said temperature is in the range of from about 130° C. to about 160° C.

5. The method of claim 1 wherein the reaction is carried out in a contained environment.

6. The method of claim 1 wherein from about 1.5 to about 20 moles of $NH_4OH$ (as ammonia) are contacted per mole of 3,4,5,6-tetrachloropicolinonitrile.

7. The method of claim 1 wherein said acidification is accomplished by the addition of sulfuric acid or hydrochloric acid.

* * * * *